(12) United States Patent
Lai et al.

(10) Patent No.: US 10,918,761 B2
(45) Date of Patent: Feb. 16, 2021

(54) SOLUTION FOR TREATING CONTACT LENS AND CONTACT LENS PACKAGING SYSTEM

(71) Applicant: PEGAVISION CORPORATION, Taoyuan (TW)

(72) Inventors: Yu-Chin Lai, Taoyuan (TW); Min-Tzong Yeh, Taoyuan (TW); Han-Yi Chang, Taoyuan (TW); Ya-Hui Chang, Taoyuan (TW)

(73) Assignee: PEGAVISION CORPORATION, Taoyuan (TW)

( * ) Notice: Subject to any disclaimer, the term of this patent is extended or adjusted under 35 U.S.C. 154(b) by 54 days.

(21) Appl. No.: 15/343,229

(22) Filed: Nov. 4, 2016

(65) Prior Publication Data

US 2017/0368222 A1 Dec. 28, 2017

(30) Foreign Application Priority Data

Jun. 27, 2016 (TW) .............................. 105120217 A

(51) Int. Cl.
*A61L 12/14* (2006.01)
*C11D 3/37* (2006.01)
*C11D 3/00* (2006.01)
*C11D 3/22* (2006.01)
*A61L 12/08* (2006.01)

(52) U.S. Cl.
CPC .............. *A61L 12/14* (2013.01); *A61L 12/08* (2013.01); *A61L 12/086* (2013.01); *C11D 3/0078* (2013.01); *C11D 3/227* (2013.01); *C11D 3/3784* (2013.01)

(58) Field of Classification Search
CPC ........ A61L 12/14; A61L 12/08; A61L 12/086; C11D 3/3784; C11D 3/0078; C11D 3/227
See application file for complete search history.

(56) References Cited

U.S. PATENT DOCUMENTS

| 2001/0044482 | A1* | 11/2001 | Hu | ........................ | C08F 265/04 |
| | | | | | 523/106 |
| 2003/0186825 | A1* | 10/2003 | Mitani | .................. | A61L 12/142 |
| | | | | | 510/112 |
| 2004/0137079 | A1 | 7/2004 | Cook et al. | | |
| 2005/0164979 | A1* | 7/2005 | Gross | .................... | A61K 31/728 |
| | | | | | 514/54 |
| 2009/0100801 | A1 | 4/2009 | Zhao et al. | | |
| 2009/0291020 | A1 | 11/2009 | Wagenaar | | |
| 2014/0102917 | A1* | 4/2014 | Mori | .................... | C11D 3/2096 |
| | | | | | 206/5.1 |
| 2015/0024987 | A1 | 1/2015 | Matsuoka et al. | | |

FOREIGN PATENT DOCUMENTS

| CN | 1602198 A | 3/2005 |
| CN | 101332308 A | 12/2008 |
| CN | 104272174 A | 1/2015 |
| EP | 3040085 A1 | 7/2016 |
| JP | 2000098310 A | 4/2000 |
| JP | 2009112260 A | 5/2009 |
| JP | 2011093897 A | 5/2011 |
| JP | 2014040598 A | 3/2014 |
| JP | 2014074010 A | 4/2014 |
| JP | 2015534106 A | 11/2015 |
| TW | 200941028 A1 | 10/2009 |

* cited by examiner

*Primary Examiner* — Matthew P Coughlin
*Assistant Examiner* — Thurman Wheeler
(74) *Attorney, Agent, or Firm* — CKC & Partners Co., LLC

(57) ABSTRACT

A solution for treating a contact lens and a contact lens packaging system are provided. The solution includes about 0.01 to about 1.0 parts by weight (pbw) of a polymer having phosphorylcholine groups, about 0.005 to about 0.05 pbw of a hydrophilic molecule, about 0.01 to about 1.0 pbw of an inorganic salt, and about 100 pbw of water. A number-average molecular weight of the polymer is about 4,000 to about 1,000,000 daltons. The polymer has a structure of formula (I):

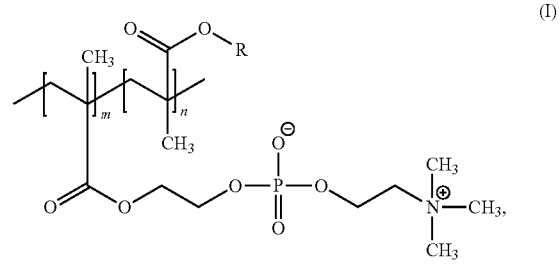

(I)

wherein, in formula (I), m is a positive integer, n is zero or a positive integer, and R is $C_2$-$C_{12}$ alkyl group, or $C_2$-$C_{12}$ hydroxyalkyl group. When n is a positive integer, m/n is greater than 1. Moreover, a number-average molecular weight of the hydrophilic molecule is about 10,000 to about 5,000,000 daltons. The hydrophilic molecule is hyaluronic acid (HA) or hyaluronate salt.

9 Claims, No Drawings

SOLUTION FOR TREATING CONTACT LENS AND CONTACT LENS PACKAGING SYSTEM

CROSS-REFERENCE TO RELATED APPLICATION

This application claims priority to Taiwan Application Serial Number 105120217, filed Jun. 27, 2016, which is herein incorporated by reference.

BACKGROUND

Field of Invention

The present invention relates to a solution for treating a contact lens and a contact lens packaging system. More particularly, the present invention relates to a solution including a polymer having phosphorylcholine groups and a hydrophilic molecular.

Description of Related Art

Soft contact lens is a kind of popular commercial product. It is packed inside a polypropylene blister package including storage solution for sale. The storage solution is usually a buffered saline solution which includes sodium chloride and other inorganic salts. In addition, it further includes surfactants and/or moisturizers to keep the contact lens moist and prevent the contact lens from sticking on the inner surface of blister-like structure of blister package.

Regarding to functions of the contact lens, the contact lens must be capable of correcting visual acuity. In addition, a comfort level of wearing contact lens would affect consumer preferences. Therefore, in the field of contact lens, people in the business target promoting the comfort level of wearing contact lens. The comfort level of wearing contact lens is affected by a lot of factors. For example, discomfort generated from wearing contact lens may be because lens is too rigid, lens has poor wettability and thus make surfaces of lens dry, surfaces of lens are rough, or lens is not well-designed. For example, the wettability of conventional hydrogel lenses is generally good; however, the materials of silicon hydrogel lenses are relatively hydrophobic and some hydrogel lenses would be added with hydrophobic UV blockers. Therefore, these silicon hydrogel lenses and the lenses including UV blockers usually have poor wettability. That is one of reasons that makes lens wearers feel uncomfortable.

However, the wettability and the comfort level of lens depend on the materials of lens. Besides, they also depend on storage solution of lens and even the components of cleaning solution. Therefore, a novel treating solution for contact lens is in need. It should be capable of promoting wettability of contact lens such that surfaces of contact lens are not easy to become dry, reducing eyestrain caused by wearing lens for long periods of time, and promoting comfort level of wearing contact lens.

BRIEF SUMMARY

The invention provides a solution for treating a contact lens. The solution includes about 0.01 to about 1.0 parts by weight (pbw) of a polymer having phosphorylcholine groups, about 0.005 to about 0.05 pbw of a hydrophilic molecule, about 0.01 to about 1.0 pbw of an inorganic salt, and about 100 pbw of water. A number-average molecular weight of the polymer is about 4,000 to about 1,000,000 daltons. The polymer has a structure of formula (I):

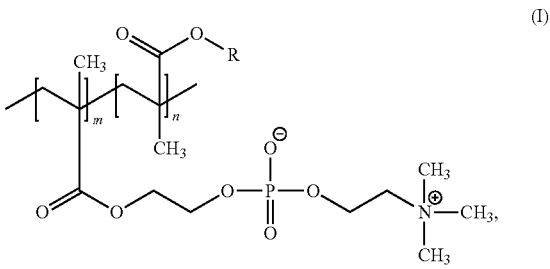

wherein, in formula (I), m is a positive integer, n is zero or a positive integer, and R is $C_2$-$C_{12}$ alkyl group, or $C_2$-$C_{12}$ hydroxyalkyl group. When n is the positive integer, m/n is greater than 1. Moreover, a number-average molecular weight of the hydrophilic molecule is about 10,000 to about 5,000,000 daltons. The hydrophilic molecule is hyaluronic acid (HA) or hyaluronate salt.

In some embodiments of the invention, the number-average molecular weight of the first hydrophilic molecule is about 10,000 to about 50,000 daltons, about 100,000 to about 400,000 daltons, or about 1,000,000 to about 5,000,000 daltons.

In some embodiments of the invention, the solution for treating the contact lens further includes about 0.005 to about 0.05 pbw of a second hydrophilic molecule. A number-average molecular weight of the second hydrophilic molecule is about 10,000 to about 50,000 daltons, about 100,000 to about 400,000 daltons, or about 1,000,000 to about 5,000,000 daltons. The second hydrophilic molecule is hyaluronic acid or hyaluronate salt.

In some embodiments of the invention, the solution for treating the contact lens further includes about 0.005 to about 0.05 pbw of a second hydrophilic molecule and about 0.005 to about 0.05 pbw of a third hydrophilic molecule. The number-average molecular weight of the first hydrophilic molecule is about 10,000 to about 50,000 daltons. A number-average molecular weight of the second hydrophilic molecule is about 100,000 to about 400,000 daltons. A number-average molecular weight of the third hydrophilic molecule is about 1,000,000 to about 5,000,000 daltons. The second hydrophilic molecule and third hydrophilic molecule are independently hyaluronic acid or hyaluronate salt.

In some embodiments of the invention, R is n-butyl, 2-ethylhexyl, isodecyl, lauryl, 2-hydroxyethyl, or 2,3-dihydroxypropyl.

In some embodiments of the invention, the inorganic salt includes sodium chloride, sodium borate, or a combination thereof.

In some embodiments of the invention, the solution for treating the contact lens further includes about 0.1 to about 1 pbw of boric acid.

The invention provides a contact lens packaging system. The contact lens packaging system includes a container, a contact lens, a solution for storing the contact lens. The solution for storing the contact lens is held in the container. The contact lens is immersed in the solution for storing the contact lens. Aforementioned solutions for treating the contact lens may be used as the solution for storing the contact lens.

In some embodiments of the invention, the contact lens includes a UV blocker.

DETAILED DESCRIPTION

The following embodiments are disclosed for detailed description. For illustration clarity, many details of practice are explained in the following descriptions. However, it should be understood that these details of practice do not intend to limit the present invention. That is, these details of practice are not necessary in parts of embodiments of the present invention. Furthermore, chemical formulas in the invention are shown with schematic illustrations.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising", or "includes" and/or "including" or "has" and/or "having" when used in this specification, specify the presence of stated features, regions, integers, steps, operations, elements, and/or components, but do not preclude the presence or addition of one or more other features, regions, integers, steps, operations, elements, components, and/or groups thereof.

In order to solve these problems mentioned previously in the background, such as, poor wettability of contact lenses, and uncomfortable feelings when wearing contact lenses. The present invention provides a solution for treating a contact lens. After immersing the contact lens in the solution or using the solution to clean the contact lens, components in the solution would enter into a lens matrix or adhere on surfaces of the lens, such that the treated lens would have relatively good wettability, thereby promoting the comfort level when wearing lens. The solution for treating the contact lens includes about 0.01 to about 1.0 parts by weight (pbw) of a polymer having phosphorylcholine groups, about 0.005 to about 0.05 pbw of a hydrophilic molecule, about 0.01 to about 1.0 pbw of an inorganic salt, and about 100 pbw of water. A number-average molecular weight of the polymer is about 4,000 to about 1,000,000 daltons. The polymer has a structure of formula (I):

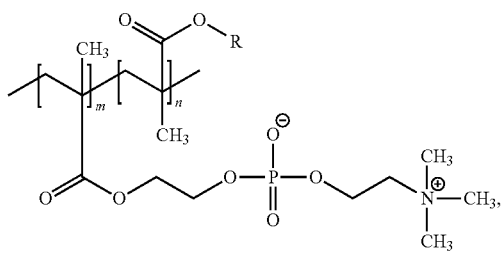

wherein, in formula (I), m is a positive integer, n is zero or a positive integer, and R is $C_2$-$C_{12}$ alkyl group, or $C_2$-$C_{12}$ hydroxyalkyl group. When n is the positive integer, m/n is greater than 1. Moreover, a number-average molecular weight of the hydrophilic molecule is about 10,000 to about 5,000,000 daltons. The hydrophilic molecule is hyaluronic acid (HA) or hyaluronate salt and they both have good hydrophilic properties. For example, the hyaluronate salt is sodium hyaluronate.

When n is zero, this polymer is a homopolymer having phosphorylcholine groups. That is, the homopolymer is poly(2-methacryloyloxyethyl phosphorylcholine)(poly-MPC). When n is a positive integer, this polymer is a copolymer having phosphorylcholine groups.

The reasons that the present invention uses the polymer having phosphorylcholine groups as one of the components of the solution for treating the contact lens are as follows. The human tear film has a trilaminar structure. The innermost layer is in direct contact with a cornea and main component of the innermost layer is water. The outermost layer is exposed to the air and includes phospholipids, which contains a portion of structure of a phosphorylcholine molecule. Therefore, the phospholipids are capable of preventing the water in the innermost layer from evaporating quickly and preventing the cornea from dryness. Because the polymer of the present invention has similar structure as the phospholipids, when the polymer is released from the lens or adheres on surfaces of the lens, it can achieve similar effects as the outermost layer of the tear film, thereby preventing the water in the tear film from evaporating quickly and thus keeping eyes moist. Because the homopolymer and the copolymer of the present invention both have phosphorylcholine groups, both of them have good moisturizing effect.

The copolymer of present invention may be copolymerized by 2-methacryloyloxyethyl phosphorylcholines (MPC) and methacrylic acid esters. For example, the methacrylic acid ester may be alkyl methacrylate or hydroxyalkyl methacrylate. The alkyl methacrylate has $C_2$-$C_{12}$ alkyl group. It may be n-butyl methacrylate (BMA), 2-ethylhexyl methacrylate (EHMA), isodecyl methacrylate (IDMA) or lauryl methacrylate (LMA). The hydroxyalkyl methacrylate has $C_2$-$C_{12}$ hydroxyalkyl group. It may be 2-hydroxyethyl methacrylate (HEMA) or 2,3-dihydroxypropyl methacrylate (DHPM). Therefore, in the polymer having the structure of formula (I), R is n-butyl, 2-ethylhexyl, isodecyl, lauryl, 2-hydroxyethyl, or 2,3-dihydroxypropyl.

Because the solution for treating the contact lens includes many kinds of components having highly hydrophilic properties, it is useful for promoting the comfort level when wearing contact lens. For example, the contact lens may be immersed in the solution for treating the contact lens, such that components in solution can enter into the lens matrix or stay near lens surface during autoclaving at high temperature. However, because of these factors, pore sizes and hydrophilicity of lens, and the difference between the polarity of lens and the polarity of components in the storage solution, the components in the storage solution have different degrees of adhesion on the surfaces of lens.

Moreover, different contact lenses are formed from combinations of different monomers and thus have different crosslinking densities. Accordingly, the ability of components of storage solution to enter or penetrate into the lens is very much dependent on the polarities and the molecular weights of these components as well as crosslinking densities of the hydrogel lens.

Therefore, by adjusting the number-average molecular weight of the first hydrophilic molecule, solutions for treating contact lenses that suitable for contact lenses with different materials can be formed. For example, the number-average molecular weight of the first hydrophilic molecule is about 10,000 to about 50,000 daltons, about 100,000 to about 400,000 daltons, or about 1,000,000 to about 5,000,000 daltons. It can be known that the solution for treating the contact lens may includes the low-molecular-weight, middle-molecular-weight or high-molecular-weight first hydrophilic molecule.

These first hydrophilic molecules with different molecular weight respectively have different uses. When the first hydrophilic molecules are released from the lens, they can enter the cornea or stay on the cornea surface. More specifically, the low-molecular-weight first hydrophilic molecule has the smallest size, thus can enter into the cornea deeply, and has the best effect of moisturizing the cornea. The middle-molecular-weight first hydrophilic molecule adheres on the cornea and can help the cornea retain water tightly. The high-molecular-weight first hydrophilic molecule has the strongest water absorbing ability and thus can retain the water on the cornea. Therefore, by using the solution including the polymer and the first hydrophilic molecule for treating the contact lens, human eyes would feel comfortable when wearing the treated contact lens.

According to some embodiment of the present invention, the solution for treating the contact lens may includes two kinds of hydrophilic molecules. For example, the solution for treating the contact lens may further includes a second hydrophilic molecule. A number of parts by weight, materials, and a number-average molecular weight of the second hydrophilic molecule can refer to the number of parts by weight, the materials, and the number-average molecular weight of the first hydrophilic molecule.

According to some embodiment of the present invention, the solution for treating the contact lens may includes three (or more) kinds of hydrophilic molecules. For example, the solution for treating the contact lens further includes a second hydrophilic molecule and a third hydrophilic molecule. The number-average molecular weight of the first hydrophilic molecule is about 10,000 to about 50,000 daltons. A number-average molecular weight of the second hydrophilic molecule is about 100,000 to about 400,000 daltons. A number-average molecular weight of the third hydrophilic molecule is about 1,000,000 to about 5,000,000 daltons. The numbers of parts by weight of the first hydrophilic molecule, the second hydrophilic molecule, and the third hydrophilic molecule are all about 0.005 to about 0.05 and are independently hyaluronic acid or hyaluronate salt. As mentioned previously, hydrophilic molecule with different molecular weights have different effects of moisturizing the cornea. Therefore, by adjusting the amount of each hydrophilic molecule, solutions for treating contact lenses may be applied for contact lenses with different materials, such that lens wearer can feel the best comfort level.

In some embodiments, the inorganic salt includes sodium chloride, sodium borate, or a combination thereof. In some embodiments, the solution for treating the contact lens further includes about 0.1 to about 1 pbw of boric acid. The boric acid and the sodium borate both are capable of adjusting the pH value of the solution and have antimicrobial activity. In some embodiments, the solution for treating the contact lens of the present invention may selectively includes surfactants and/or moisturizers.

The solution for treating the contact lens of the present invention can be used for storing the contact lens or cleaning the contact lens. In other words, the solution for treating the contact lens of the present invention is a contact lens storage solution, namely packaging solution, or a contact lens cleaning solution. Therefore, the present invention provides a contact lens packaging system. The packaging system includes a container, a contact lens, and a solution for storing the contact lens. The solution for storing the contact lens is held in the container. The contact lens is immersed in the solution for storing the contact lens. In some embodiments, the container is a blister and the contact lens is a soft contact lens, such as silicon hydrogel lens.

In some embodiments, the contact lens can be polymerized by ethylenically-based polymerizable monomers and prepolymers including silicon. Common polymers for forming contact lenses include N-vinyl pyrrolidone (NVP), N,N-dimethyl acrylamide (DMA), 2-methacryloyloxyethyl phosphorylcholine (MPC), different kinds of alkyl methacrylate, different kinds of hydroxyalkyl methacrylate, and so on.

In some embodiments, the contact lens includes a UV blocker. For example, the UV blocker is a monomer having a structure similar to benzophenone, a monomer having a structure similar to benzotriazole, a monomer having a structure similar to 2-hydroxyphenyl-s-triazine, or a combination thereof.

For example, the monomer having the structure similar to benzophenone includes 4-methacryloxy-2-hydroxy benzophenone or 4-(2-acryloxyethoxy-2-hydroxy benzophenone.

For example, the monomer having the structure similar to benzotriazole includes 2-(2-hydroxy-5-methacryloxyethylphenyl)-2H-benzotriazole), 2-(2-hydroxy-5-methacryloxyethylphenyl)-2H-6-chloro-benzotriazole, 2-(2-hydroxy-5-methacryloxyethylphenyl)-2H-6-methoxybenzotriazole, 2-[3'-t-butyl-5'-(3"-dimethylvinylsilylpropoxy)-2'-hydroxyphenyl]-5-methoxybenzotriazole, 2-[3'-t-butyl-5'-(3"-methacryloylozypropyl)phenyl]-5-chlorobenzotriazole, or 2-[2'-hydroxy-5'-(γ-methacryloyloxypropoxy)-3'-tert-butylphenyl]-5-methoxy-2H-benzotriazole.

For example, the monomer having the structure similar to 2-hydroxyphenyl-s-triazine includes 4-methacryloxyethyl-2-hydroxyphenyl-s-triazine, or 4-acryloxyethyl-2-hydroxyphenyl-s-triazine.

Because the contact lens is immersed in the solution for storing the contact lens, the wettability of the lens can be promoted by treating with the solution. Therefore, when wearing the lens, uncomfortable feelings caused by UV blockers can be improved.

The following Examples are provided to illustrate certain aspects of the present disclosure and to aid those of skill in the art in practicing this disclosure.

These Examples are in no way to be considered to limit the scope of the disclosure in any manner.

Experiment 1: Preparing Homopolymer Having Phosphorylcholine Groups—poly(2-methacryroyloxyethylphosphoryl-choline (MPC) to Obtain Examples 1A-1C The Experiment 1 included the following steps. 50 g (0.169 moles) of MPC and 150 mL of methanol were added into a three-neck round-bottom flask equipped with a reflux condenser. Nitrogen gas was injected into the three-neck round-bottom flask. The MPC and the methanol were stirred under the nitrogen-filled environment for 10 minutes until dissolution. Subsequently, 0.25 g of azobisisobutyronitrile (AIBN) and 0.0398 g (0.509 mmoles) of 2-mercaptoethanol were added and then heated to 45° C. maintaining for 24 hours. The AIBN is a polymerization initiator and it can bond to the carbon atom which is connected with double bonds in methacryloyloxyethyl of MPC to initiate free radical polymerization. The 2-mercaptoethanol is a chain transfer agent and it is capable of making the terminals of chain polymer having radical terminate reaction and thus the length and the molecule weight (number-average molecular weight and weight-average molecular weight) of a polymer can be controlled. After that, the methanol was stripped. The formed product, poly-MPC (Example 1A), was crushed into powder and dried in an oven at 100° C. for 6 hours. Through this experiment, 45 g of poly-MPC (Example 1A), which is MPC homopolymer, was produced. It was characterized by gel permeation chromatography (GPC) to obtain the number-average molecular weight ($M_n$) and the weight-average molecular weight ($M_w$).

The number-average molecular weight ($M_n$) can be obtained by measuring the molecular mass of n polymer molecules, summing the masses, and dividing by n. The weight-average molecular weight ($M_w$) can be obtained by measuring each polymer molecule's molecular weight, multiplying each molecular weight with each polymer molecule's weight percent relative to the total weight of all polymer molecules, and summing these products. Because when calculating the $M_n$, the weights of polymer molecules with different numbers of monomers are same; however, when calculating the $M_w$, the weights of heavier polymer molecules are larger, $M_w$ of polymers is usually larger than $M_n$. The ratio of $M_w$ to $M_n$ is polydispersity. Generally, if adding less 2-mercaptoethanol during polymerization, the polydispersity would be higher. It shows that the distribution of molecular weights of polymers is wider. The standard deviation between the numbers of monomers in polymers is larger.

Other homopolymers were also made by the method described above but the amount of each reacts was different. In details, the preparation of MPC homopolymers included the following steps. 59 g (0.1999 moles) of MPC and 250 mL of methanol were added into a three-neck round-bottom flask equipped with a reflux condenser. Nitrogen gas was injected into the three-neck round-bottom flask. The MPC and the methanol were stirred under the nitrogen-filled environment for 10 minutes until dissolution. Subsequently, 0.295 g of azobisisobutyronitrile (AIBN) and 2-mercaptoethanol were added and then heated to 45° C. maintaining for 24 hours. The amount of 2-mercaptoethanol was 0.2343 g (3 mmoles) or 0.0398 g (0.5 mmoles). Therefore, due to different amounts of 2-mercaptoethanol, the final products, Example 1B and Example 1C, could be produced respectively. After that, the methanol was stripped. The formed products, poly-MPCs (Example 1B and Example 1C), were dried in an oven at 100° C. for 6 hours. The MPC homopolymers produced by the experiment were characterized by GPC to obtain number-average molecular weights ($M_n$) and weight-average molecular weights ($M_w$).

Examples 1A-1C have a structure of formula (II) as follows:

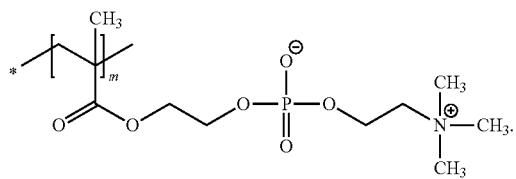

(II)

In formula (II), m is a positive integer and * is the starting point of the polymerization. That is, * is the position connecting with AIBN.

Experiment 2: Preparing Copolymer Having Phosphorylcholine Groups to Obtain Examples 2A-2D MPC copolymers were also made by the method described above but MPC copolymers were polymerized by different kinds of hydroxyalkyl methacrylate monomers. Moreover, the amount of each reactant was different. In details, the preparation of MPC polymers included the following steps. 48 g (0.163 moles) of MPC, 12 g (0.092 moles) of 2-hydroxyethyl methacrylate (HEMA), and 250 mL of methanol were added into a three-neck round-bottom flask equipped with a reflux condenser. Nitrogen gas was injected into the three-neck round-bottom flask. The MPC, the HEMA and the methanol were stirred under the nitrogen-filled environment for 10 minutes until dissolution. Subsequently, 0.295 g of azobisisobutyronitrile (AIBN) and 2-mercaptoethanol were added and then heated to 45° C. maintaining for 24 hours. The amount of 2-mercaptoethanol was 0.932 g (0.012 moles), 0.2343 g (3 mmoles), or 0.0469 g (0.06 mmoles). Therefore, due to different amounts of 2-mercaptoethanol, the final products, Example 2A, Example 2B, and Example 2C, could be produced respectively. After that, the methanol was stripped. The formed products, MPC-HEMA copolymers (Examples 2A-2C), namely poly(MPC-co-HEMA)s, were dried in an oven at 100° C. for 6 hours. The MPC-HEMA copolymers produced by the experiment were characterized by GPC to obtain number-average molecular weights (Me) and weight-average molecular weights ($M_w$).

The results characterized by GPC show that: Example 2A, which was formed from HEMA and 0.012 moles of 2-mercaptoethanol, has a number-average molecular weight ($M_n$) of 13,341, a weight-average molecular weight ($M_w$) of 21,438, and a polydispersity of 1.607. Example 2B, which was formed from HEMA and 3 mmoles of 2-mercaptoethanol, has a number-average molecular weight ($M_n$) of 29,326, a weight-average molecular weight ($M_w$) of 123,345, and a polydispersity of 4.206. Example 2C, which was formed from HEMA and 0.06 mmoles of 2-mercaptoethanol, has a number-average molecular weight ($M_n$) of 106,978, a weight-average molecular weight ($M_w$) of 721,246, and a polydispersity of 6.742. Examples 2A-2C have a structure of formula (III) as follows:

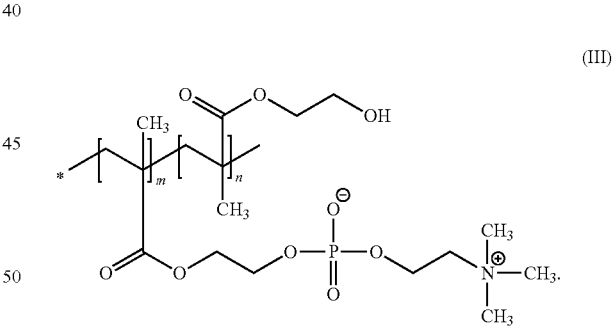

(III)

In formula (III), m and n are positive integers and * is the starting point of the polymerization. That is, * is the position connecting with AIBN.

Further, Example 2D was also made by the method described above. However, the HEMA was replaced with 5 g (0.0352 moles) of n-butyl methacrylate (BMA) and the amount of AIBN was adjusted to 0.1 g, the amount of 2-mercaptoethanol was adjusted to 0.0615 g (0.8 mmoles), the amount of methanol was adjusted to 284 mL. MPC-BMA copolymer (Example 2D), namely poly(MPC-co-BMA), could be produced.

Example 2D, which was formed from BMA and 0.8 mmoles of 2-mercaptoethanol, has a number-average molecular weight ($M_n$) of 35,041, a weight-average molecular weight ($M_w$) of 74,286, and a polydispersity of 2.12. Example 2D has a structure of formula (IV) as follows:

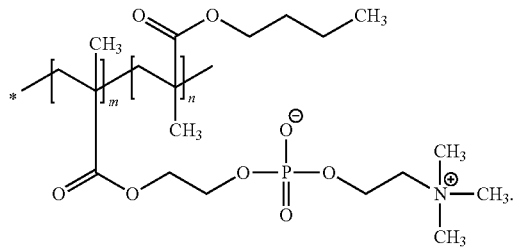

(IV)

In formula (IV), m and n are positive integers and * is the starting point of the polymerization. That is, * is the position connecting with AIBN.

The reactants used for producing Examples 1A-1C and 2A-2D and the molecular weights and the polydispersities of Examples 1A-1C and 2A-2D are all listed in the following Table 1:

average molecular weight of 30,000, 0.06% w/w of hyaluronic acid which has a number-average molecular weight of 100,000, 0.0075% w/w of hyaluronic acid which has a number-average molecular weight of 1,000,000, 0.1% w/w of Example 1A (poly-MPC), and water as solvent.

Experiment 4: Etafilcon a Lens Treated with Different Lens Storage Solutions

This experiment was performed by immersing etafilcon A lenses in the storage solutions of Comparative Example 3A and Example 3C respectively. Monomers for forming etafilcon A lenses included 2-hydroxyethyl methacrylate (HEMA), methacrylic acid (MAA), ethylene glycol dimethacrylate (EGDMA), 1,1,1-trimethylolpropane trimethacrylate (TMPTMA), and about 0.8% of UV blocking monomer, 2(2-hydroxy-5-methacryloxyethylphenyl)-2H-benzotriazole. These monomers were solidified in molds to form lenses. The lenses can be designed to have different curvatures by cast molding with different shapes of polypropylene molds. The formed lenses would have targeted optical powers ranging from −6.00 to −2.00 dipoters, 8.5 mm base curve (BC), and 14.2 mm diameter. After proper

TABLE 1

| | Example 1A | Example 1B | Example 1C | Example 2A | Example 2B | Example 2C | Example 2D |
|---|---|---|---|---|---|---|---|
| MPC | 50 g (0.169 mole) | 59 g (0.1999 mole) | 59 g (0.1999 mole) | 48 g (0.163 mole) | 48 g (0.163 mole) | 48 g (0.163 mole) | 45 g (0.153 mole) |
| HEMA | — | — | — | 12 g (0.092 mole) | 12 g (0.092 mole) | 12 g (0.092 mole) | — |
| BMA | — | — | — | — | — | — | 5 g (0.0352 mole) |
| 2-Mercaptoethanol | 0.0398 g (0.509 mmole) | 0.2343 g (3 mmole) | 0.0398 g (0.5 mmole) | 0.932 g (0.012 mole) | 0.2343 g (3 mmole) | 0.0469 g (0.06 mmole) | 0.0615 g (0.8 mmole) |
| AIBN | 0.25 g | 0.295 g | 0.295 g | 0.295 g | 0.295 g | 0.295 g | 0.1 g |
| Methanol | 150 mL | 250 mL | 250 mL | 250 mL | 250 mL | 250 mL | 284 mL |
| Number-average molecular weight ($M_n$) | 9,604 | 17,646 | 47,121 | 13,341 | 29,326 | 106,978 | 35,041 |
| Weight-average molecular weight ($M_w$) | 31,935 | 45,791 | 206,531 | 21,438 | 123,345 | 721,246 | 74,286 |
| Polydispersity | 3.32 | 2.595 | 4.383 | 1.607 | 4.206 | 6.742 | 2.12 |

Experiment 3: Preparing Lens Storage Solutions Including MPC Homopolymers and the First Hydrophilic Molecule This experiment was performed by selectively adding Example 1A (poly-MPC), hyaluronic acid, and a combination thereof to form three different contact lens storage solutions, namely Comparative Example 3A and Examples 3B-3C. Components of each of Comparative Example 3A and Examples 3B-3C are listed as follows.

Comparative Example 3A included 0.708% w/w of sodium chloride, 0.470% w/w of boric acid, 0.05% w/w of sodium borate, 0.06% w/w of hyaluronic acid which has a number-average molecular weight of 100,000, and water as solvent.

Example 3B included 0.708% w/w of sodium chloride, 0.470% w/w of boric acid, 0.05% w/w of sodium borate. 0.06% w/w of hyaluronic acid which has a number-average molecular weight of 100,000, 0.1% w/w of Example 1A (poly-MPC), and water as solvent.

Example 3C included 0.708% w/w of sodium chloride, 0.470% w/w of boric acid, 0.05% w/w of sodium borate, 0.0075% w/w of hyaluronic acid which has a numberhydration process, they were packed in polypropylene blisters with Comparative Example 3A and Example 3C, respectively. Subsequently, lenses were sterilized with autoclaving. These parameters and powers of the fully processed lenses would meet their targets and the fully processed lenses would have water content of 58%.

Experiment 5: Clinical Trials of Etafilcon a Lenses Treated by Different Storage Solution After satisfying the requirements of regulations of clinical trials, etafilcon A lenses treated by Comparative Example 3A and Example 3C respectively were tested in clinical trials. Over 30 subjects were instructed to wear lenses for at least 10 hours without leaving an air conditioned environment at a temperature of 25° C. and a humidity of 60%. The test included the following steps. On the first day, the subjects wore lenses treated by Comparative Example 3A the whole day. On the second day, the subjects wore lenses treated by Example 3C the whole day. By alternatively wearing different treated lenses, the subjects could compare the comfort levels after wearing different treated lenses.

After wearing the lenses which had been immersed in Comparative Example 3A over 6 hours, over 70% of the subjects felt that their eyes are dry. However, under the same conditions, after the subjects wearing the lenses which had been immersed in Example 3C, no one felt dry. Such results obviously showed that the poly-MPC and the hyaluronic acid with different molecular weights in storage solution could effectively keep lenses moist and prevent wearer's eyes from feeling dry. This result also proved that the moisturizing and anti-drying effects of the poly-MPC and the hyaluronic acid with different molecular weights are much better than the hyaluronic acid only with single molecular weight. Moreover, even though the etafilcon A lenses include the UV blocker, the copolymers formed by MPC would also effectively keep lenses moist and thus promote the comfort level of wearer.

Experiment 6: Lubricity Tests of Etafilcon a Lenses Treated by Different Storage Solution Lubricity tests of etafilcon A lens in AcuVueMoist and etafilcon A lenses treated by Comparative Example 3A and Example 3C respectively were performed. The AcuVueMoist is a kind of commercial product and includes a packaging solution containing polyvinylpyrrolidone (PVP) and an etafilcon A lens immersed in the packaging solution. The experimental procedure was as follows. One etafilcon A lens was taken out from the AcuVueMoist. The other two etafilcon A lenses were immersed in Comparative Example 3A and Example 3C respectively and taken out subsequently. These three etafilcon A lenses were disposed on a slope and then slid down the slope. The lens treated by Example 3C slid fastest. The lens of AcuVueMoist is slower than the lens treated by Example 3C. The lens treated by Comparative Example 3A slid slowest. It could be seen that surfaces of the lens treated by Example 3C had the best lubricity. Therefore, the friction between the surfaces and the slope was the smallest during sliding process. That proved that the solution for treating the contact lens of the present invention can effectively lubricate the surfaces of the contact lens.

Experiment 7: Comparing the Different Required Time of Water Film Breaking on Surfaces of Etafilcon a Lenses Treated by Different Storage Solution The different required time of water film breaking on surfaces of etafilcon A lenses treated by different storage solution was compared. The experimental procedure was as follows. One etafilcon A lens was taken out from the AcuVueMoist. The other two etafilcon A lenses were immersed in Comparative Example 3A and Example 3C respectively and taken out subsequently. The time from taking out the lens to the water film breaking on surfaces of lens was recorded. The time of water film breaking on surfaces of etafilcon A lens of the AcuVueMoist was about 85 seconds. The time of water film breaking on surfaces of etafilcon A lens treated by Example 3C was about 80 seconds. The time of water film breaking on surfaces of etafilcon A lens treated by Comparative Example 3A was about 73 seconds. It could be seen that the solution for treating the contact lens effectively promoted the water-retaining ability of the surfaces of the lens.

Experiment 8: Comparing the Evaporation Rates of Water in Etafilcon a Lenses Treated by Different Storage Solution The different evaporation rates of water in etafilcon A lens of the AcuVueMoist and in etafilcon A lenses treated by Comparative Example 3A and Example 3C were compared. The experimental procedure was as follows. One etafilcon A lens was taken out from the AcuVueMoist. The other two etafilcon A lenses were immersed in Comparative Example 3A and Example 3C respectively and taken out subsequently. The water content of each lens varying with time after taking out the lens in the above steps was recorded. The experimental results were listed in Table 2 as follows:

TABLE 2

| | Lens of AcuVueMoist | Lens treated by Comparative Example 3A | Lens treated by Example 3C |
|---|---|---|---|
| Water content after 1 hour (%) | 36% | 20% | 41% |
| Water content after 2 hours (%) | 5% | 3% | 12% |
| Water content after 2.5 hour (%) | 4% | 0% | 8% |
| Water content after 3 hour (%) | 3% | 0% | 5% |
| Water content after 4 hour (%) | 1% | 0% | 5% |

From the Table 2, it could be seen that the water contents of the lenses would gradually decrease after the lenses being taken out from the storage solutions. The water content of the lens treated by Comparative Example 3A decreased fastest. After the lens being taken out for 2.5 hours, the water content of the lens was 0%. The water content of the lens treated by Example 3C decreased slowest. After the lens being taken out for 4 hours, the lens still had the water content of 5%. It could prove that the solution for treating the contact lens of the present invention could retain water in the lens and thus keep the lens moist Therefore, when wearing a lens treated by the solution for treating the contact lens of the present invention, because of the high water content of the lens, the comfort level of lens wearer can be promoted.

Based on the above test results, it can be seen that the solution for treating the contact lens of the present invention can effectively lubricate the lens and retain water in the lens, such that the uncomfortable feelings caused by hydrophobic silicon hydrogel materials and the UV blocker can be improved and thus lens wearer would feel comfortable and the eyestrain would not occur easily.

Although the present invention has been described in considerable detail with reference to certain embodiments thereof, other embodiments are possible. Therefore, the spirit and scope of the appended claims should not be limited to the description of the embodiments contained herein.

It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims.

What is claimed is:

1. A solution for treating a contact lens, comprising:

about 0.01 to about 1.0 parts by weight (pbw) of a polymer having phosphorylcholine groups, a number-average molecular weight of the polymer being about 4,000 to about 1,000,000 daltons, and the polymer consisting essentially of the following structure:

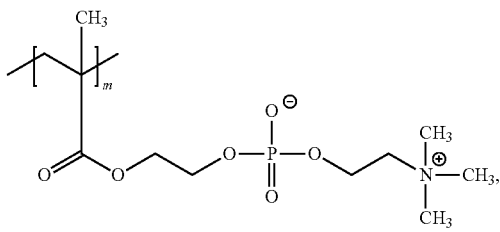

wherein m is a positive integer;

about 0.005 to about 0.05 pbw of a first hydrophilic molecule, a number-average molecular weight of the first hydrophilic molecule being about 10,000 to about 50,000 daltons, and the first hydrophilic molecule being hyaluronic acid (HA) or hyaluronate salt;

about 0.005 to 0.05 pbw of a second hydrophilic molecule, a number-average molecular weight of the second hydrophilic molecule being 100,000 to 400,000 daltons, and the second hydrophilic molecule being hyaluronic acid or hyaluronate salt;

about 0.005 to 0.05 pbw of a third hydrophilic molecule, a number-average molecular weight of the third hydrophilic molecule being 1,000,000 to 5,000,000 daltons, and the third hydrophilic molecule being hyaluronic acid or hyaluronate salt;

about 0.01 to about 1.0 pbw of an inorganic salt; and about 100 pbw of water.

2. The solution of claim 1, wherein the inorganic salt comprises sodium chloride, sodium borate, or a combination thereof.

3. The solution of claim 1, further comprising about 0.1 to about 1 pbw of boric acid.

4. A contact lens packaging system, comprising:

a container;

a solution held in the container, comprising:

about 0.01 to about 1.0 pbw of a polymer having phosphorylcholine groups, a number-average molecular weight of the polymer being about 4,000 to about 1,000,000 daltons, and the polymer having a structure of formula (I):

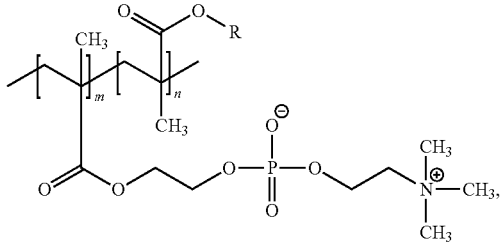

wherein, in formula (I), m is a positive integer, n is zero or a positive integer, R is $C_2$-$C_{12}$ alkyl group, or $C_2$-$C_{12}$ hydroxyalkyl group, and m/n is greater than 1 when n is the positive integer;

about 0.005 to about 0.05 pbw of a first hydrophilic molecule, a number-average molecular weight of the first hydrophilic molecule being about 10,000 to about 5,000,000 daltons, and the first hydrophilic molecule being hyaluronic acid (HA) or hyaluronate salt;

about 0.01 to about 1.0 pbw of an inorganic salt; and about 100 pbw of water; and a contact lens immersed in the solution.

5. The contact lens packaging system of claim 4, wherein the number-average molecular weight of the first hydrophilic molecule is about 10,000 to about 50,000 daltons, about 100,000 to about 400,000 daltons, or about 1,000,000 to about 5,000,000 daltons.

6. The contact lens packaging system of claim 5, further comprising about 0.005 to about 0.05 pbw of a second hydrophilic molecule, a number-average molecular weight of the second hydrophilic molecule being about 10,000 to about 50,000 daltons, about 100,000 to about 400,000 daltons, or about 1,000,000 to about 5,000,000 daltons, and the second hydrophilic molecule being hyaluronic acid or hyaluronate salt.

7. The contact lens packaging system of claim 4, further comprising about 0.005 to about 0.05 pbw of a second hydrophilic molecule and about 0.005 to about 0.05 pbw of a third hydrophilic molecule, the number-average molecular weight of the first hydrophilic molecule being about 10,000 to about 50,000 daltons, a number-average molecular weight of the second hydrophilic molecule being about 100,000 to about 400,000 daltons, a number-average molecular weight of the third hydrophilic molecule being about 1,000,000 to about 5,000,000 daltons, and the second hydrophilic molecule and third hydrophilic molecule being independently hyaluronic acid or hyaluronate salt.

8. The contact lens packaging system of claim 4, wherein the contact lens comprises a UV blocker.

9. A solution for treating a contact lens, comprising:

about 0.01 to about 1.0 parts by weight (pbw) of a polymer having phosphorylcholine groups, a number-average molecular weight of the polymer being about 4,000 to about 1,000,000 daltons, and the polymer consisting essentially of a structure of formula (I):

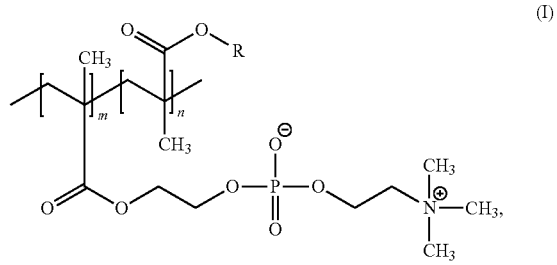

wherein, in formula (I), m is a positive integer, n is zero or a positive integer, R is $C_2$-$C_{12}$ hydroxyalkyl group, and m/n is greater than 1 when n is the positive integer;

about 0.005 to about 0.05 pbw of a first hydrophilic molecule, a number-average molecular weight of the first hydrophilic molecule being about 10,000 to about 30,000 daltons, and the first hydrophilic molecule being hyaluronic acid or hyaluronate salt;

about 0.005 to 0.05 pbw of a second hydrophilic molecule, a number-average molecular weight of the second hydrophilic molecule being 100,000 to 400,000 daltons, and the second hydrophilic molecule being hyaluronic acid or hyaluronate salt;
about 0.005 to 0.05 pbw of a third hydrophilic molecule, a number-average molecular weight of the third hydrophilic molecule being 1,000,000 to 5,000,000 daltons, and the third hydrophilic molecule being hyaluronic acid or hyaluronate salt;
about 0.01 to about 1.0 pbw of an inorganic salt; and
about 100 pbw of water.

* * * * *